(12) United States Patent
Nishijima

(10) Patent No.: US 11,311,268 B2
(45) Date of Patent: Apr. 26, 2022

(54) X-RAY CT APPARATUS

(71) Applicant: CANON MEDICAL SYSTEMS CORPORATION, Otawara (JP)

(72) Inventor: Akira Nishijima, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 16/983,420

(22) Filed: Aug. 3, 2020

(65) Prior Publication Data
US 2021/0038182 A1   Feb. 11, 2021

(30) Foreign Application Priority Data

Aug. 7, 2019   (JP) .............................. JP2019-145608

(51) Int. Cl.
*A61B 6/04* (2006.01)
*G01R 33/20* (2006.01)
*A61B 6/00* (2006.01)
*G01R 31/382* (2019.01)
*A61B 6/03* (2006.01)

(52) U.S. Cl.
CPC ................ *A61B 6/56* (2013.01); *A61B 6/035* (2013.01); *A61B 6/486* (2013.01); *A61B 6/54* (2013.01); *G01R 31/382* (2019.01)

(58) Field of Classification Search
CPC ......... A61B 6/035; A61B 6/56; A61B 6/4405; A61B 6/032; A61B 6/52; A61B 6/563; A61B 5/055; A61B 1/00; A61B 6/03
See application file for complete search history.

(56) References Cited

U.S. PATENT DOCUMENTS

2012/0256099 A1* 10/2012 Gregerson ............. A61B 6/035
250/453.11

FOREIGN PATENT DOCUMENTS

| EP | 2 893 875 A1 | 7/2015 |
|----|--------------|--------|
| JP | 10-66689 A | 3/1998 |
| JP | 2011-161017 A | 8/2011 |
| WO | WO 2014/038421 A1 | 3/2014 |

* cited by examiner

*Primary Examiner* — Don K Wong
(74) *Attorney, Agent, or Firm* — Oblon, McClelland, Maier & Neustadt, L.L.P.

(57) ABSTRACT

An X-ray CT apparatus of an embodiment includes an X-ray tube, an X-ray detector, a data processor, a battery, a rotating body, and processing circuitry. The X-ray detector is configured to detect X rays output from the X-ray tube. The data processor is configured to process a signal output from the X-ray detector. The battery is configured to supply electric power to the data processor. The rotating body is configured to rotatably support the X-ray tube and the X-ray detector, the X-ray tube facing the X-ray detector, and further to rotatably support the data processor and the battery. The processing circuitry is configured to monitor a remaining capacity of the battery, and determine a scanning condition on the basis of the remaining capacity.

12 Claims, 13 Drawing Sheets

X-RAY CT APPARATUS

CROSS-REFERENCE TO RELATED APPLICATION

The present application claims priority based on Japanese Patent Application No. 2019-145608, filed on Aug. 7, 2019, the content of which is incorporated herein by reference.

FIELD

Embodiments of the present invention relate to an X-ray CT apparatus.

BACKGROUND

An X-ray computed tomography (CT) apparatus includes a rotating body on which an X-ray tube device, an X-ray detector, and the like are provided and images an examination subject by radiating X rays to the examination subject while rotating around the examination subject according to a rotation mechanism of the rotating body. Power supply to the rotating body is performed in such a manner that a power supply device provided in a fixed part of a gantry applies a high voltage to the rotating body through a slip ring, for example.

As described above, the technology in the related art requires a slip ring for power supply to the rotating body. However, since abrasion of a metal part or the like occurs in the slip ring during supply of electricity, there are cases in which maintenance such as regular removal of abrasion debris and exchange of parts is required.

DETAILED DESCRIPTION

Hereinafter, an X-ray CT apparatus of an embodiment will be described with reference to the drawings. The X-ray CT apparatus of the embodiment includes a battery which supplies electric power to a rotating body of a gantry. The remaining capacity of the battery is monitored by a console device or the like and a scanning protocol and the like in response to the remaining capacity is presented to an operator. A scanning protocol includes information such as imaging conditions, contrast radiography conditions, and an image display method of the X-ray CT apparatus. It is possible to reduce the number of maintenance man-hours and costs for replacement of a slip ring, and the like by driving the rotating body using the battery. In addition, it is possible to prevent the picture quality of a scanned image from deteriorating due to noise generated during power supply because a switching power supply or the like is not necessary.

An X-ray CT apparatus of an embodiment includes an X-ray tube, an X-ray detector, a data processor, a battery, a rotating body, and processing circuitry. The X-ray detector is configured to detect X rays output from the X-ray tube. The data processor is configured to process a signal output from the X-ray detector. The battery is configured to supply electric power to the data processor. The rotating body is configured to rotatably support the X-ray tube and the X-ray detector, the X-ray tube facing the X-ray detector, and further to rotatably support the data processor and the battery. The processing circuitry is configured to monitor a remaining capacity of the battery, and determine a scanning condition on the basis of the remaining capacity. Thereby, it is possible to reduce the number of man-hours and costs of maintenance by eliminating a slip ring.

Overall Configuration

Figure 1:
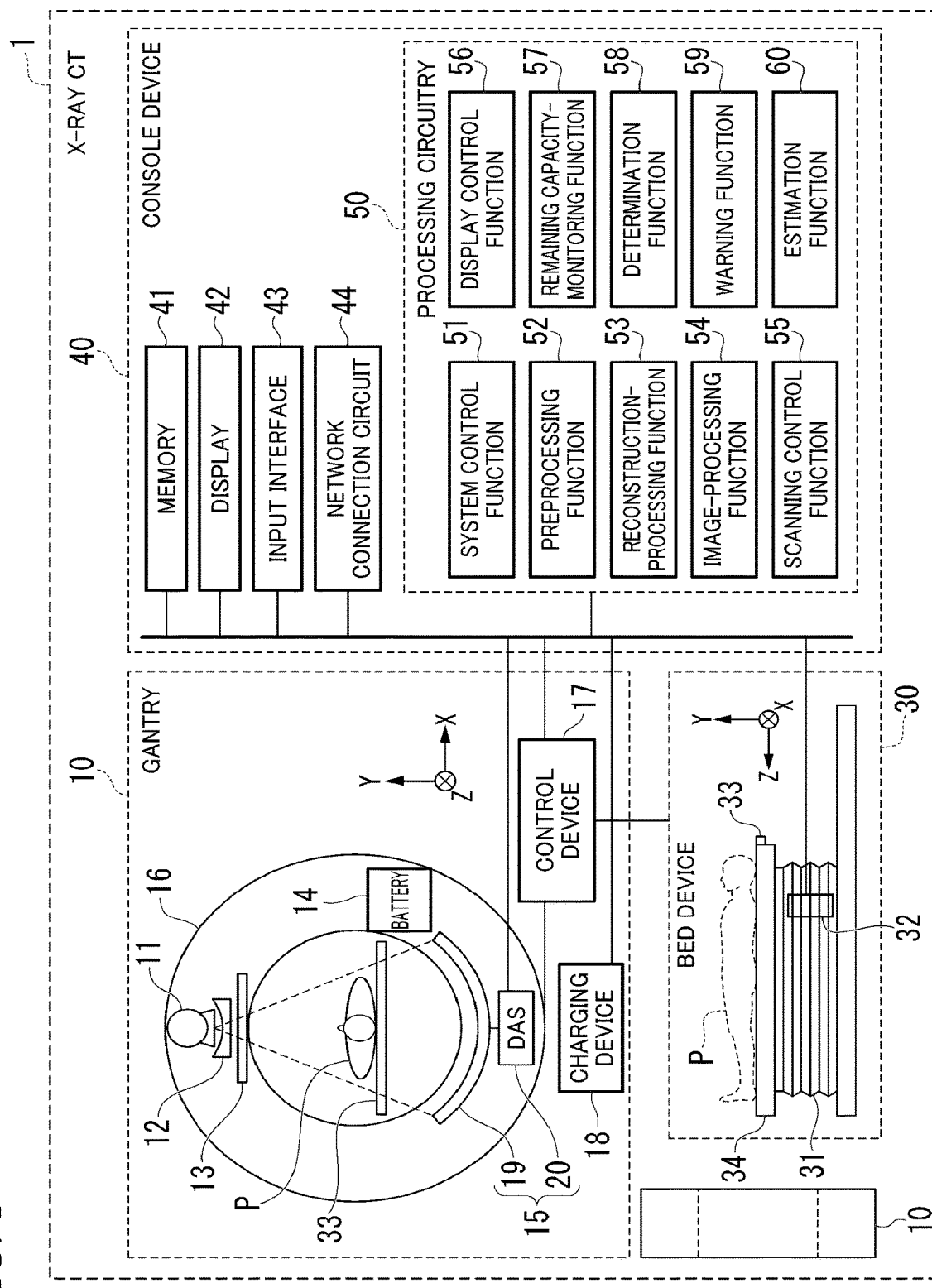
FIG. 1 is a configuration diagram of an X-ray CT apparatus 1 according to an embodiment.

FIG. 1 is a configuration diagram of an X-ray CT apparatus 1 according to the embodiment. The X-ray CT apparatus 1 includes, for example, a gantry 10, a bed device 30, and a console device 40. Although FIG. 1 shows both a diagram of the gantry 10 viewed in a Z-axis direction and a diagram viewed in an X-axis direction for convenience of description, there is actually only one gantry 10. In the embodiment, a rotation axis of a rotary frame 16 in a non-tilted state or a longitudinal direction of a top board 33 of the bed device 30 is defined as a Z-axis direction, an axis at a right angle to the Z-axis direction that is parallel to the floor is defined as an X-axis direction, and a direction at a right angle to the Z-axis direction that is perpendicular to the floor is defined as a Y-axis direction.

The gantry 10 includes, for example, an X-ray tube 11, a wedge 12, a collimator 13, a battery 14, a detection device 15, a rotary frame 16 (an example of a rotating body), a control device 17, and a charging device 18. The detection device 15 includes, for example, an X-ray detector 19 and a data collection system (hereinafter, a data acquisition system (DAS)) 20 (an example of a data processor).

The X-ray tube 11 generates X rays by radiating thermions from a cathode (filament) to an anode (target) according to application of a high voltage from the battery 14. The X-ray tube 11 includes a vacuum tube. For example, the X-ray tube 11 may be a rotating anode type X-ray tube which generates X rays by radiating thermions to a rotating anode. When a high-voltage generation device having an electric circuit including a transformer (trans), a rectifier, and the like is provided on the side of a fixed frame (not shown) of the gantry 10, the X-ray tube 11 may generate X rays on the basis of a high voltage supplied from the high-voltage generation device.

The wedge 12 is a filter for controlling the amount of X rays to be radiated from the X-ray tube 11 to an examination subject P. The wedge 12 attenuates X rays transmitted through the wedge 12 such that a distribution of the amount of X rays to be radiated from the X-ray tube 11 to the examination subject P becomes a predetermined distribution. The wedge 12 is also called a wedge filter or a bow-tie filter. For example, the wedge 12 may be manufactured by processing aluminum such that it has a predetermined target angle and a predetermined thickness.

The collimator 13 is a mechanism for narrowing a field of view (FOV) of X rays that have been transmitted through the wedge 12. The collimator 13 narrows the FOV of X rays, for example, by forming a slit according to combination of a plurality of lead plates. The collimator 13 may also be called an X-ray aperture.

The battery 14 is a large capacity battery such as a lithium-ion battery or an all-solid battery, for example. The battery 14 supplies electric power accumulated therein to each device provided in the rotary frame 16. The battery 14 is provided such that it is charged with electric power supplied from the charging device 18 when scanning is not executed, for example, when the X-ray CT apparatus 1 is idle. For example, the battery 14 is provided in the detection device 15 provided in the rotary frame 16, a rotating body of the rotary frame 16 (a support other than the detection device 15), or the like. A case in which the battery 14 is provided in the detection device 15 will be exemplified in the following description.

Figure 2:
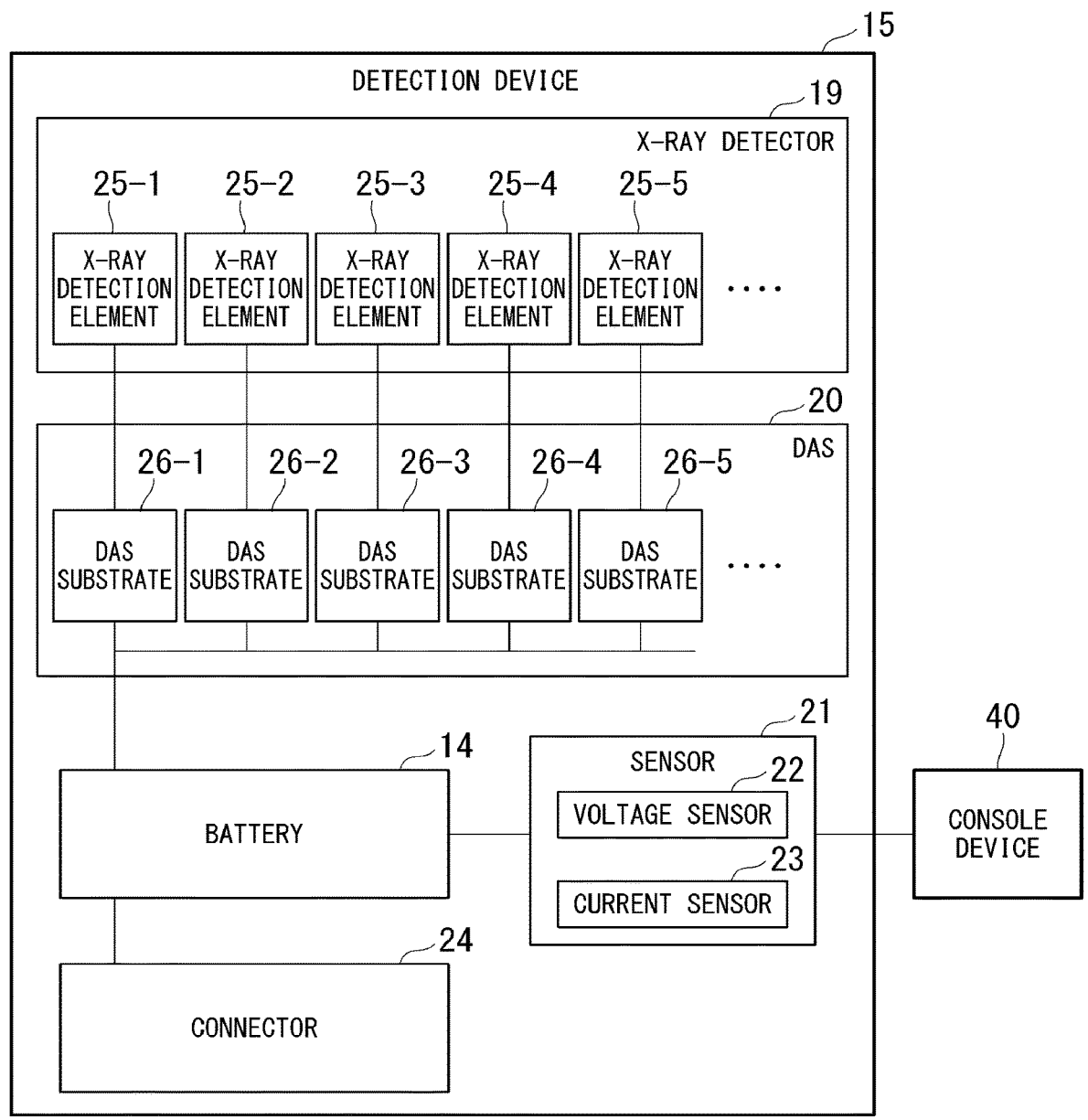
FIG. 2 is a diagram showing an example of a detection device 15 according to the embodiment.

The detection device 15 detects X rays that have been generated by the X-ray tube 11, have passed through the examination subject P, and enter therein, and outputs detection data to the console device 40. FIG. 2 is a diagram showing an example of the detection device 15. The detection device 15 includes, for example, the X-ray detector 19, the DAS 20, the battery 14, a sensor 21, and a first connector 24. The sensor 21 includes, for example, a voltage sensor 22 and a current sensor 23.

The X-ray detector 19 detects the intensity of X rays that have been generated by the X-ray tube 11, have passed through the examination subject P, and enter therein. The X-ray detector 19 outputs an electrical signal (an optical signal or the like is also possible) in response to the detected intensity of X rays to the DAS 20. The X-ray detector 19 includes, for example, a string of a plurality of X-ray detection elements 25 (25-1 to 25-5 and the like). Although five X-ray detection elements 25-1 to 25-5 are shown in FIG. 2, the number of X-ray detection elements is arbitrary. When the X-ray detection elements 25-1 to 25-5 are not distinguished from one another, they will be simply referred to as an "X-ray detection element 25" in the following.

The plurality of X-ray detection elements 25 are obtained by arranging a plurality of X-ray detection elements in a channel direction along an arc having the focus of the X-ray tube 11 as a center. The string of the plurality of X-ray detection elements 25 is arranged in a slice direction (row direction).

Each of the plurality of X-ray detection elements 25 is, for example, an indirect detector including a grid, a scintillator array and an optical sensor array. The scintillator array includes a plurality of scintillators. Each scintillator has scintillator crystals. Scintillator crystals emit an amount of light in response to the intensity of incident X rays. The grid is disposed on a surface of the scintillator array to which X rays are input and includes an X-ray shielding plate having a function of absorbing scattered X rays. There is a case in which the grid is called a collimator (one-dimensional collimator or two-dimensional collimator). The optical sensor array includes, for example, optical sensors such as Si photodiodes. The optical sensor array outputs an electrical signal in response to the amount of light emitted from the scintillators. The X-ray detector 19 may be a direct conversion type detector including a semiconductor element which converts incident X rays into an electrical signal.

The DAS 20 includes, for example, a plurality of DAS substrates 26 (26-1 to 26-5 and the like). Although five DAS substrates 26-1 to 26-5 are shown in FIG. 2, the number of DAS substrates is arbitrary. When the DAS substrates 26-1 to 26-5 are not distinguished from one another, they will be simply referred to as a "DAS substrate 26" in the following.

Each of the plurality of DAS substrates 26 includes, for example, an amplifier, an integrator, and an A/D converter. The amplifier performs amplification processing on an electrical signal output from each X-ray detection element 25 of the X-ray detector 19. The integrator integrates amplified electrical signals over a view period. The A/D converter converts an electrical signal representing an integration result into a digital signal. The DAS 20 outputs detection data based on the digital signal to the console device 40. The detection data is a digital value of an X-ray intensity identified through a channel number and a string number of an X-ray detection element that is a generation source, and a view number indicating a collected view. A view number is a number that varies according to rotation of the rotary frame 16 and is, for example, a number that increments according to rotation of the rotary frame 16. Accordingly, the view number is information representing a rotation angle of the X-ray tube 11. A view period is a period from a rotation angle associated with a certain view number to a rotation angle associated with the next view number. The DAS 20 may detect view switching through a timing signal input from the control device 17, an internal timer, or a signal acquired from a sensor which is not shown. When X rays are continuously emitted by the X-ray tube 11 during full scanning, the DAS 20 collects detection data groups associated with the entire circumference (360 degrees). When X rays are continuously emitted by the X-ray tube 11 during half scanning, the DAS 20 collects detection data associated with half a circumference (180 degrees).

The sensor 21 acquires data for measuring the remaining capacity of the battery 14 and transmits the acquired data to the console device 40. The remaining capacity is an index value indicated by a state of charge (SOC), for example. The sensor 21 includes, for example, the voltage sensor 22 and the current sensor 23. The voltage sensor 22 detects a voltage value of the battery 14. A voltage detected by the voltage sensor 22 is, for example, an open-circuit voltage (OCV). The voltage sensor 22 transmits data representing a detected voltage value to the console device 40. The current sensor 23 detects a current value of charging/discharging current of the battery 14. The current sensor 23 transmits data representing a detected current value to the console device 40. The console device 40 calculates a remaining capacity of the battery 14 on the basis of the received voltage value data and current value data.

The first connector 24 connects the battery 14 and the charging device 18 when charging of the battery 14 is performed. The first connector 24 is connected to a connector on the side of the charging device 18 when scanning is not executed (when scanning is stopped), for example, when the X-ray CT apparatus 1 is idle. A charging method through the first connector 24 will be described in detail later.

Referring back to FIG. 1, the rotary frame 16 is an annular member which rotatably supports the X-ray tube 11, the wedge 12, the collimator 13 and the X-ray detector 19 such that the X-ray tube 11, the wedge 12 and the collimator 13 face the X-ray detector 19. The rotary frame 16 is rotatably supported by a fixed frame having the examination subject P introduced thereinto as a center. Additionally, the rotary frame 16 rotatably supports the battery 14 and the DAS 20. Detection data output from the DAS 20 is transmitted from a transmitter having a light-emitting diode (LED) provided in the rotary frame 16 to a receiver having a photodiode provided in a non-rotary part (e.g., a fixed frame) of the gantry 10 through optical communication and forwarded to the console device 40 through the receiver. A method of transmitting detection data from the rotary frame 16 to a non-rotary part is not limited to the aforementioned method using optical communication and any non-contact type transmission method may be employed. The rotary frame 16 is not limited to an annular member and may be a member such as an arm as long as it can support and rotate the X-ray tube 11 and the like.

Figure 3:
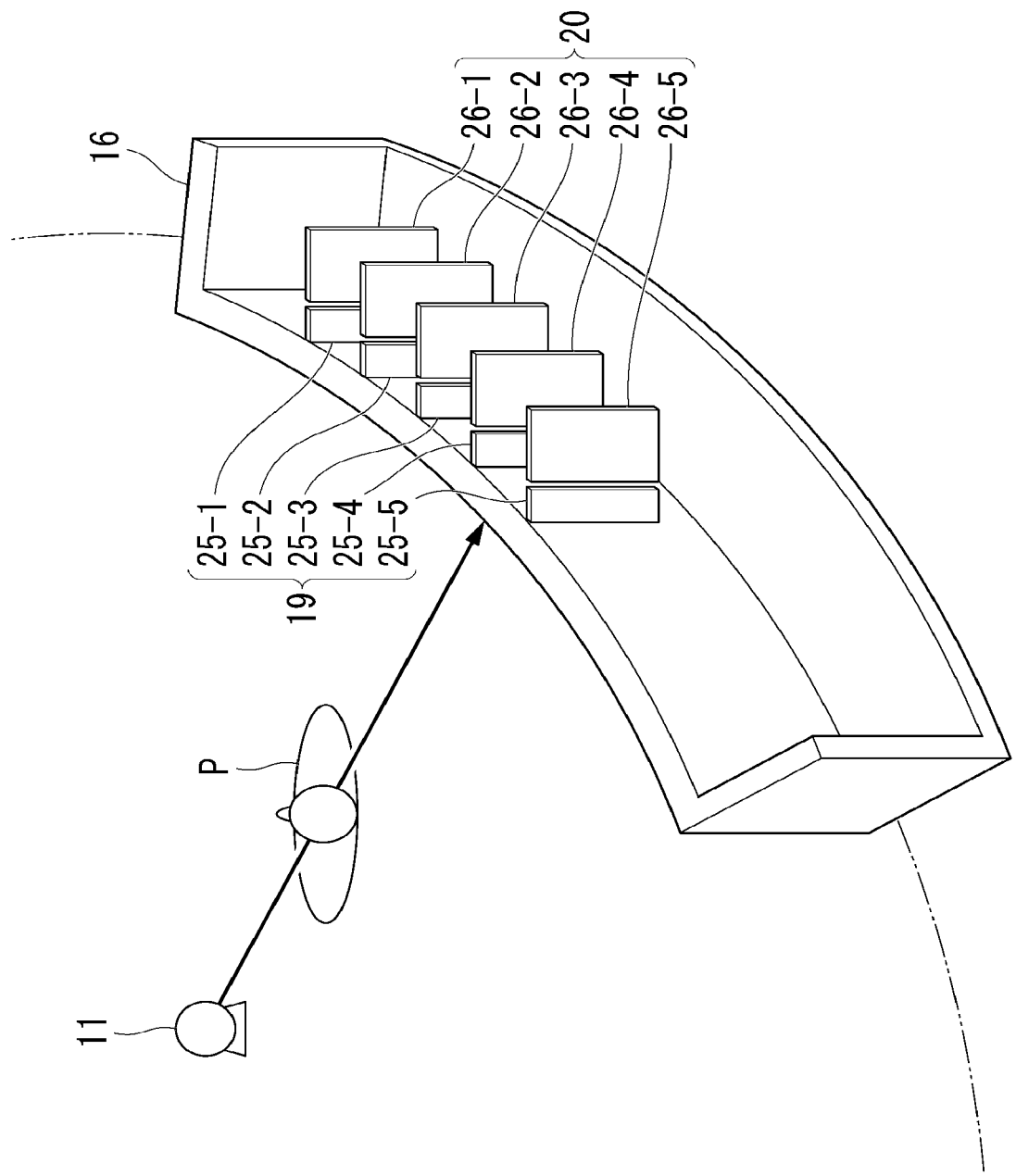
FIG. 3 is a diagram showing a state in which an X-ray detector 19 and a DAS 20 are supported by a rotary frame 16 according to the embodiment.

FIG. 3 is a diagram showing a state in which the X-ray detector 19 and the DAS 20 are supported by the rotary frame 16. The X-ray detection element 25 detects X rays that have been output from the X-ray tube 11 and have passed through the examination subject P. The DAS substrate 26 processes an electrical signal output from the X-ray detection element 25 and outputs detection data that is a processing result to the console device 40. As shown in FIG. 3, the DAS substrate 26 is supported by being inserted into a slot provided in the rotary frame 16.

Although the X-ray CT apparatus 1 may be, for example, a Rotate/Rotate-Type X-ray CT apparatus (third-generation CT) in which both the X-ray tube 11 and the X-ray detector 19 are supported by the rotary frame 16 and rotate around the examination subject P, it is not limited thereto and may be a Stationary/Rotate-Type X-ray CT apparatus (fourth-generation CT) in which a plurality of X-ray detection elements arranged in an annular shape are fixed to a fixed frame and the X-ray tube 11 rotates around the examination subject P.

Referring back to FIG. 1, the control device 17 includes, for example, processing circuitry having a processor such as a central processing unit (CPU) and a driving mechanism including a motor, an actuator and the like. The control device 17 receives an input signal from an input interface 43 attached to the console device 40 or the gantry 10 and controls operations of the gantry 10 and the bed device 30.

For example, the control device 17 may rotate the rotary frame 16, tilt the gantry 10 or move the top board 33 of the bed device 30. In addition, the control device 17 controls an output voltage of the battery 14 in response to the amount of X rays to be generated by the X-ray tube 11. When the control device 17 tilts the gantry 10, the control device 17 rotates the rotary frame 16 on an axis parallel to the Z-axis direction on the basis of an inclination angle (tilt angle) input to the input interface 43. The control device 17 ascertains a rotation angle of the rotary frame 16 through an output of a sensor which is not shown, and the like. In addition, the control device 17 provides the rotation angle of the rotary frame 16 to processing circuitry 50 (an example of a controller) at any time. The control device 17 may be provided in the gantry 10 or provided in the console device 40.

The charging device 18 charges the battery 14 provided in the rotary frame 16. The charging device 18 is disposed in a fixed part of the X-ray CT apparatus 1. The charging device 18 is connected to the detection device 15 when scanning is not executed, for example, when the X-ray CT apparatus 1 is idle and charges the battery 14 by supplying electric power to the battery 14 provided in the detection device 15. For example, the charging device 18 may transform AC power supplied from a commercial power supply or the like into DC power and supply the DC power to the battery 14. A charging method of the charging device 18 will be described in detail later.

The bed device 30 moves the examination subject P to be scanned mounted thereon and introduces the examination subject P into the rotary frame 16 of the gantry 10. The bed device 30 includes, for example, a base 31, a bed-driving device 32, the top board 33, and a supporting frame 34. The base 31 includes a housing which supports the supporting frame 34 such that the supporting frame 34 can move in a vertical direction (Y-axis direction). The bed-driving device 32 includes a motor and an actuator. The bed-driving device 32 moves the top board 33 on which the examination subject P is mounted in the longitudinal direction (Z-axis direction) of the top board 33 along the supporting frame 34. The top board 33 is a plate-shaped member on which the examination subject P is mounted.

The bed-driving device 32 may move the supporting frame 34 in the longitudinal direction of the top board 33 as well as the top board 33. Further, contrary to the above, the gantry 10 may be movable in the Z-axis direction and the rotary frame 16 may be controlled such that it comes near the examination subject P in accordance with movement of the gantry 10. In addition, both the gantry 10 and the top board 33 may be configured such that they are movable. Furthermore, the X-ray CT apparatus 1 may be a type of apparatus in which the examination subject P is scanned in a standing position or a sitting position. In this case, the X-ray CT apparatus 1 has an examination subject supporting mechanism instead of the bed device 30 and the gantry 10 rotates the rotary frame 16 in an axial direction perpendicular to the floor.

The console device 40 includes, for example, a memory 41, a display 42, the input interface 43, a network connection circuit 44, and the processing circuitry 50. Although the console device 40 is described as a body separate from the gantry 10 in the embodiments, some or all components of the console device 40 may be included in the gantry 10.

The memory 41 is realized, for example, by a semiconductor element such as a random access memory (RAM) or a flash memory, a hard disk, an optical disc, or the like. The memory 41 stores, for example, detection data, projection data, reconstructed images (CT images), a scanning plan, scanned images, and the like. Such data may be stored in an external memory with which the X-ray CT apparatus 1 can communicate instead of the memory 41 (or in addition to the memory 41). For example, the external memory may be controlled through a cloud server which manages the external memory by receiving a read request. The external memory is realized, for example, by a system called picture archiving and communication systems (PACS). PACS systematically store images captured by various image diagnostic apparatuses, and the like.

The display 42 displays various types of information. For example, the display 42 displays medical images (CT images) generated by the processing circuitry 50, graphical user interface (GUI) images through which various operations from an operator are received, and the like. For example, the display 42 may be a liquid crystal display, a cathode ray tube (CRT), an organic electroluminescence (EL) display, or the like. The display 42 may be provided in the gantry 10. The display 42 may be a desktop type or a display device (e.g., a tablet terminal) which can wirelessly communicate with the main body of the console device 40.

The input interface 43 receives various input operations from an operator and outputs electrical signals representing details of received input operations to the processing circuitry 50. For example, the input interface 43 may receive operations of inputting collection conditions when detection data or projection data is collected, reconstruction conditions when a CT image is reconstructed, image processing conditions when a postprocessing image is generated from a CT image, and the like. For example, the input interface 43 may be realized by a mouse, a keyboard, a touch panel, a trackball, a switch, a button, a joystick, a camera, an infrared sensor, a microphone, or the like. The input interface 43 may be provided in the gantry 10. In addition, the input interface 43 may be realized by a display device (e.g., a tablet terminal) which can wirelessly communicate with the main body of the console device 40.

The network connection circuit 44 includes, for example, a network card having a printed circuit board, a wireless communication module, or the like. The network connection circuit 44 implements an information communication protocol in accordance with the form of a network to be connected thereto. The network may include, for example, a local area network (LAN), a wide area network (WAN), the Internet, a cellular network, a dedicated line, and the like.

The processing circuitry 50 controls the overall operation of the X-ray CT apparatus 1. The processing circuitry 50 executes, for example, a system control function 51, a preprocessing function 52, a reconstruction-processing function 53, an image-processing function 54, the scanning control function 55, a display control function 56, a remaining capacity-monitoring function 57 (an example of a "remaining capacity monitor"), a determination function 58 (an example of a "determiner"), a warning function 59 (an example of a "warner"), an estimation function 60 (an example of an "estimator"), and the like. For example, the processing circuitry 50 realizes these functions by a hardware processor executing a program stored in the memory 41.

The hardware processor refers to, for example, a circuit (circuitry) such as a CPU, a graphics processing unit (GPU), an application specific integrated circuit (ASIC), a programmable logic device (e.g., a simple programmable logic device (SPLD)), a complex programmable logic device (CPLD), or a field programmable gate array (FPGA). The program may be directly incorporated into the circuit of the hardware processor instead of being stored in the memory 41. In this case, the hardware processor realizes functions by reading and executing the program incorporated into the circuit. The hardware processor is not limited to a configuration as a single circuit and may be configured as a single hardware processor by combining a plurality of independent circuits to realize respective functions. Furthermore, a plurality of components may be integrated into a single hardware processor to realize respective functions.

Components included in the console device 40 or the processing circuitry 50 may be distributed and realized by a plurality of pieces of hardware. The processing circuitry 50 may be realized by a processing device which can communicate with the console device 40 instead of being included in the console device 40. For example, the processing device may be a workstation connected to a single X-ray CT apparatus or a device (e.g., a cloud server) which is connected to a plurality of X-ray CT apparatuses and integrally executes processes equivalent to those of the processing circuitry 50 which will be described below. That is, the configuration of the present embodiment may be realized as an X-ray CT system (medical diagnostic system) in which an X-ray CT apparatus and another processing device are connected via a network.

The system control function 51 controls various functions of the processing circuitry 50 on the basis of input operations received through the input interface 43, for example.

The preprocessing function 52 performs preprocessing such as logarithmic conversion processing, offset correction processing, inter-channel sensitivity correction processing, beam hardening correction, and correction processing using calibration data on detection data output from the DAS 20 to generate projection data and stores the generated projection data in the memory 41. The correction processing using calibration data may be performed by the reconstruction-processing function 53.

The reconstruction-processing function 53 performs reconstruction processing using a filter correction reverse projection method, a sequential approximation reconstruction method or the like on projection data generated by the preprocessing function 52 to generate a reconstructed image and stores the generated reconstructed image in the memory 41.

The image-processing function 54 converts a reconstructed image into a three-dimensional image or section image data with an arbitrary section through a known method on the basis of an input operation received through the input interface 43. Conversion into a three-dimensional image may be performed by the preprocessing function 52.

The scanning control function 55 instructs the DAS 20, the control device 17 and the bed-driving device 32 to control detection data collection processing in the gantry 10. The scanning control function 55 controls operation of each component when imaging for collecting calibration data is performed at the time of capturing positioning images, main capture images, and images used for diagnosis.

The display control function 56 controls a display mode of the display 42. For example, the display control function 56 controls the display 42 such that it displays a CT image generated by the processing circuitry 50, a GUI image through which various operations of an operator are received, and the like.

The remaining capacity-monitoring function 57 calculates and monitors the remaining capacity of the battery 14 on the basis of current value data and voltage value data of the battery 14 received from the detection device 15. The remaining capacity-monitoring function 57 calculates a SOC of the battery 14, for example, on the basis of an open-circuit voltage of the battery 14 and an integrated value of the charging/discharging current of the battery 14. For example, the remaining capacity-monitoring function 57 may calculate the SOC on the basis of a correlation between an OCV and the SOC represented by an SOC-OCV map.

The determination function 58 determines scanning conditions on the basis of the remaining capacity of the battery 14 calculated by the remaining capacity-monitoring function 57. For example, the determination function 58 may determine candidates for executable scanning protocols. For example, the determination function 58 may determine whether scanning parameters included in an executable scanning protocol are applicable.

The warning function 59 causes the display 42 to display a warning when the determination function 58 determines that scanning conditions scheduled to be executed cannot be implemented. An operator can confirm that the scanning conditions scheduled to be executed cannot be implemented by checking display of the warning.

The estimation function 60 estimates change in the remaining capacity of the battery 14 when a scanning protocol scheduled to be executed is executed on the basis of the remaining capacity of the battery 14 calculated by the remaining capacity-monitoring function 57 and the scanning protocol scheduled to be executed. For example, the estimation function 60 may estimate a time at which the remaining capacity of the battery 14 reaches a predetermined threshold value (e.g., zero), an operating time until the remaining capacity reaches zero, and the like.

According to the above-described configuration, the X-ray CT apparatus 1 scans the examination subject P in a scanning mode such as a helical scan, conventional scanning or step-and-shoot. The helical scanning is a mode of rotating the rotary frame 16 while moving the top board 33 to scanning the examination subject P in a spiral form. The conventional scanning is a mode of rotating the rotary frame 16 in a state in which the top board 33 is stopped to scanning the examination subject P in a circular orbit. The conventional scanning is then executed. The step-and-shoot is a mode of moving the position of the top board 33 at specific intervals to perform the conventional scanning in a plurality of scanning areas.

Contact Type Charging Method

Figure 4:
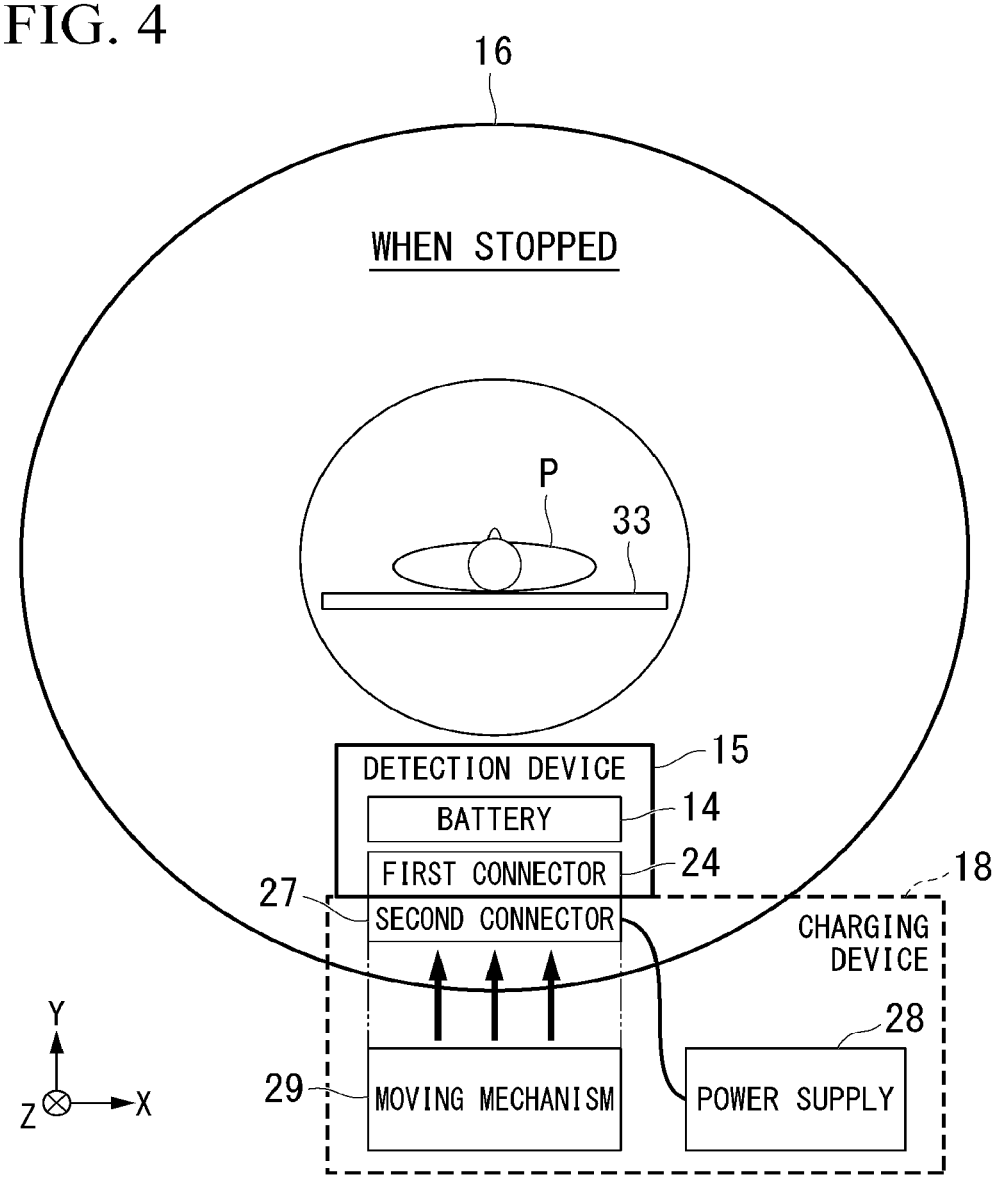
FIG. 4 is a diagram showing a state when charging is performed in a contact type charging device 18 according to the embodiment.

FIG. 4 is a diagram showing a state when charging is performed in the contact type charging device 18. The battery 14 provided in the detection device 15 is charged by receiving electric power supplied from the charging device 18 when scanning is not executed, for example, when the X-ray CT apparatus 1 is idle. When scanning is not executed, for example, when the X-ray CT apparatus 1 is idle, the detection device 15 provided in the rotary frame 16 stops at a position (hereinafter referred to as a "home position") at which power supply from the charging device 18 can be received. The first connector 24 provided in the detection device 15 is connected to a second connector 27 provided in the charging device 18 at the home position. For example, the second connector 27 may be moved to a contact position with respect to the first connector 24 according to a moving mechanism 29 which performs arm driving or the like and detachably connected to the first connector 24. Alternatively, magnetic materials may be used as materials of the first connector 24 and the second connector 27 such that the second connector 27 is attracted to the first connector 24 positioned at the home position according to a magnetic force and connected to the first connector 24.

Figure 5:
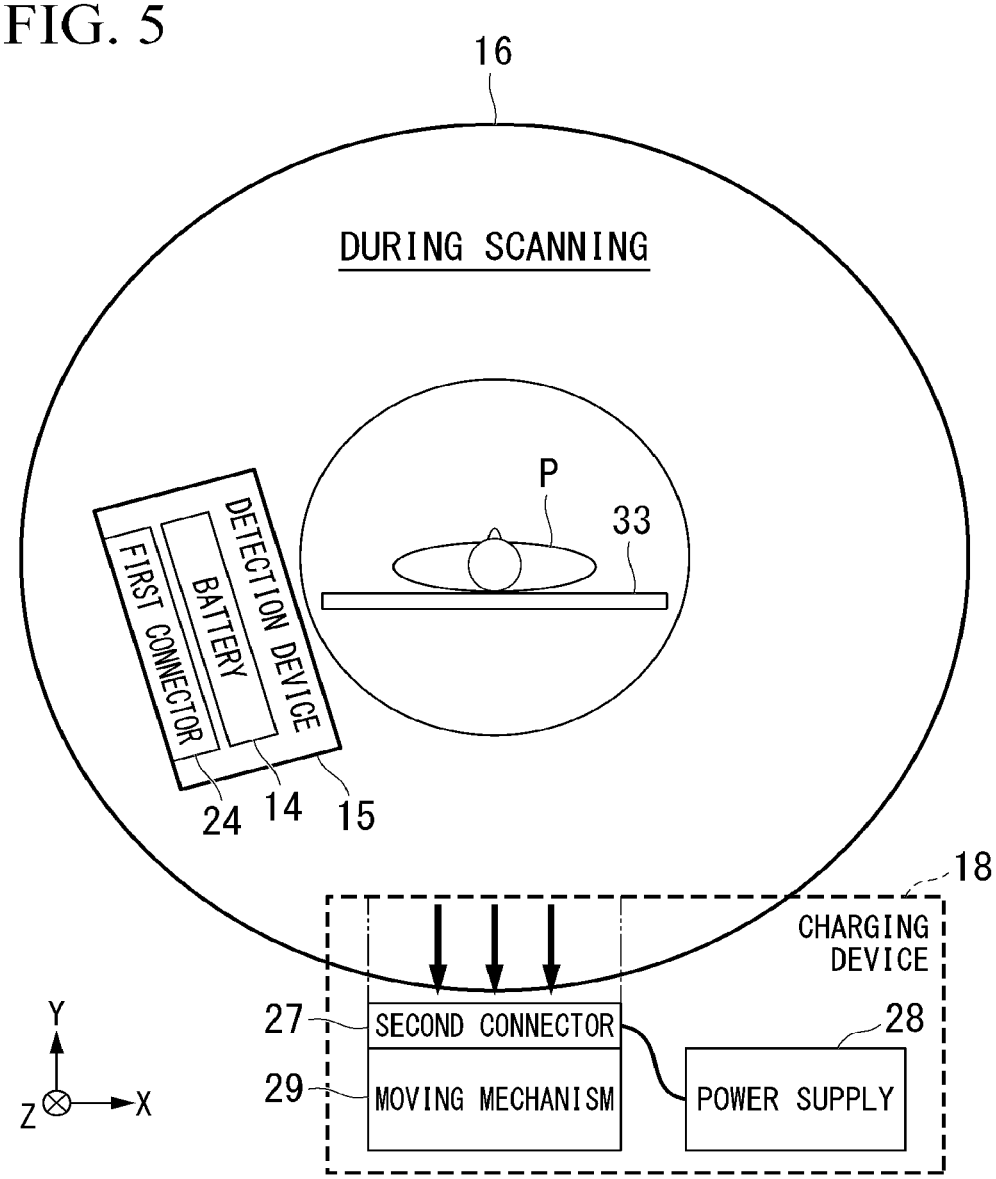
FIG. 5 is a diagram showing a state when charging is not performed in the contact type charging device 18 according to the embodiment.

FIG. 5 is a diagram showing a case when charging is not performed in the contact type charging device 18. The battery 14 provided in the detection device 15 is not charged, for example, while scanning of the X-ray CT apparatus 1 is executed. For example, the detection device 15 provided in the rotary frame 16 is separated from the charging device 18 while scanning of the X-ray CT apparatus 1 is executed, and thus the detection device 15 does not receive power supply from the charging device 18. The second connector 27 is moved to a non-contact position with respect to the first connector 24 according to the moving mechanism 29 and separated from the rotary frame 16 while scanning of the X-ray CT apparatus 1 is executed. Alternatively, when a magnetic force is used for connection of the first connector 24 and the second connector 27, the second connector 27 may be disposed at a position (position separate from the first connector 24) at which it is not attracted to the first connector 24 while scanning of the X-ray CT apparatus 1 is executed. Further, the first connector 24 and the second connector 27 may employ a configuration using an electromagnet or the like which can control generation of a magnetic force.

Contactless Type Charging Method

Figure 6:
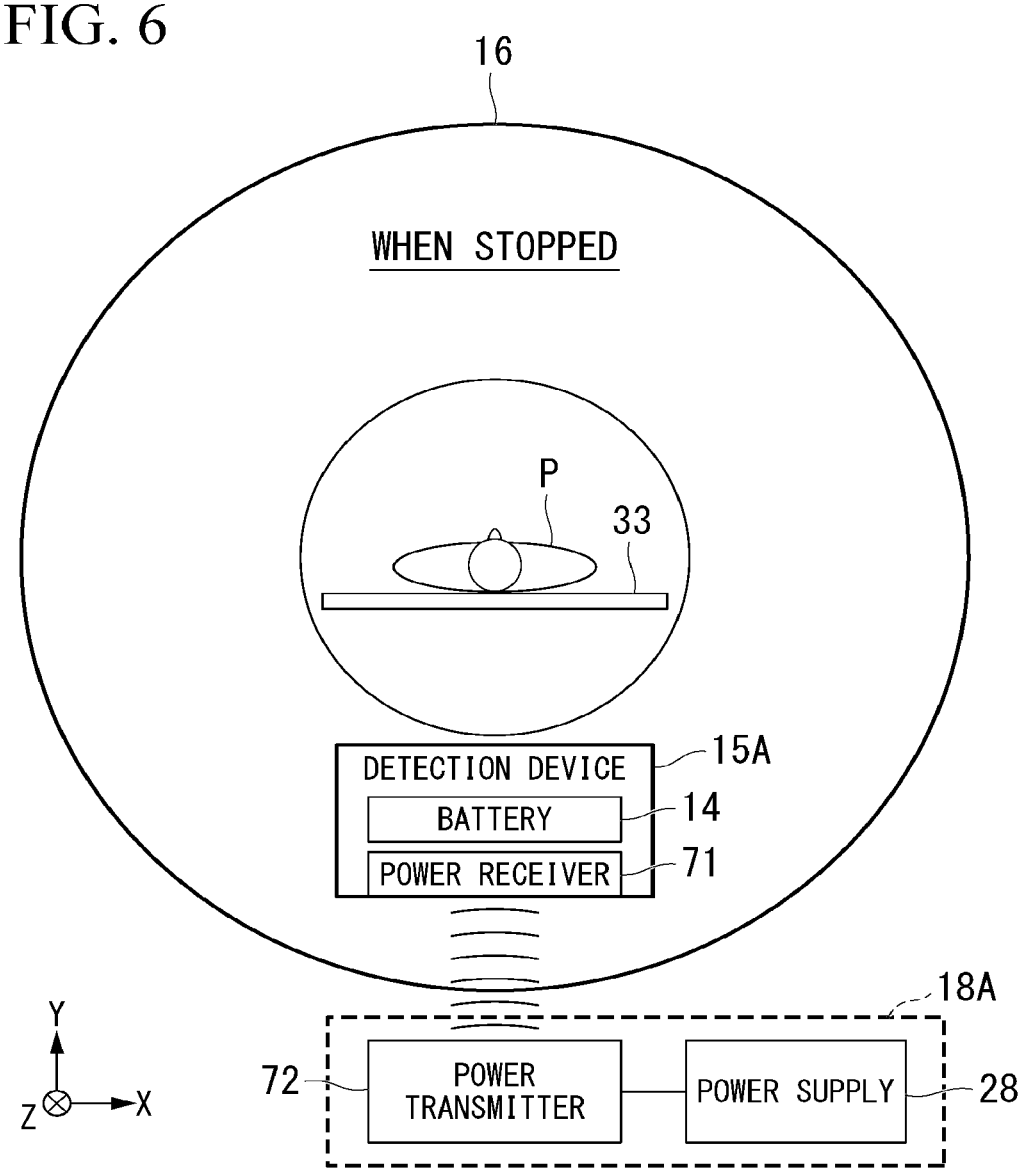
FIG. 6 is a diagram showing a state when charging is performed in a contactless type charging device 18A according to the embodiment.

FIG. 6 is a diagram showing a case when charging is performed in a contactless type charging device 18A. The battery 14 provided in a detection device 15A is charged by receiving electric power supplied from the charging device 18A when scanning is not executed, for example, when the X-ray CT apparatus 1 is idle. For example, the charging device 18A includes a power transmitter 72 having a power transmission coil. Further, the detection device 15A includes a power receiver 71 having a power reception coil. When scanning is not executed, for example, when the X-ray CT apparatus 1 is idle, the detection device 15A provided in the rotary frame 16 stops at the home position. When the detection device 15A is positioned at this home position, current flows through the power transmitter 72 of the charging device 18A to generate magnetic fields therearound. The power receiver 71 of the detection device 15A generates electric power according to the influence of the magnetic fields generated by the power transmitter 72 and supplies the generated electric power to the battery 14. Accordingly, the battery 14 is charged by receiving electric power supply.

Figure 7:
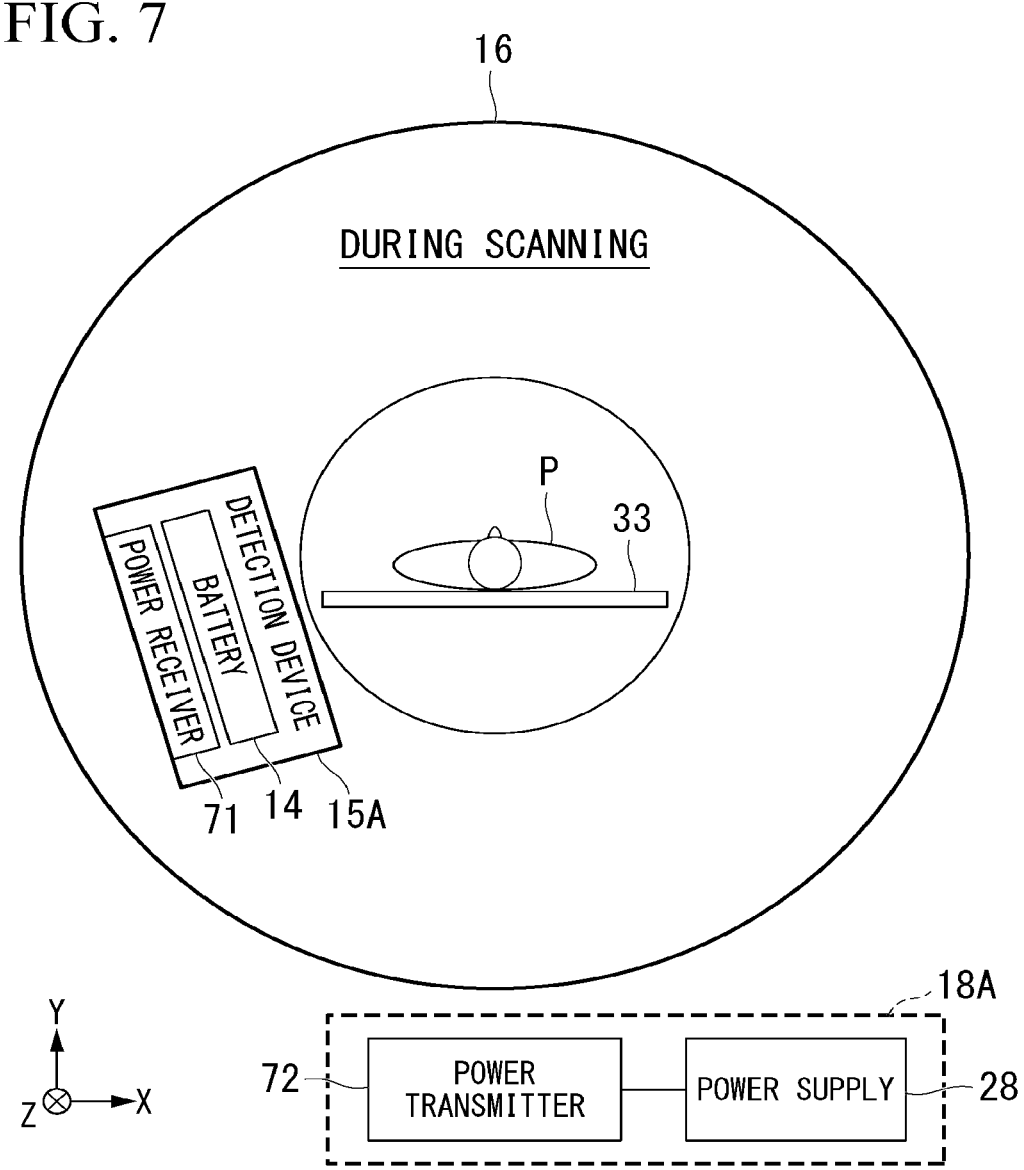
FIG. 7 is a diagram showing a state when charging is not performed in the contactless type charging device 18A according to the embodiment.

FIG. 7 is a diagram showing a case when charging is not performed in the contactless type charging device 18A. The battery 14 provided in the detection device 15A is not charged, for example, while scanning of the X-ray CT apparatus 1 is executed. For example, the detection device 15A provided in the rotary frame 16 is separated from the charging device 18A while scanning of the X-ray CT apparatus 1 is executed. Accordingly, the detection device 15A does not receive power supply from the charging device 18A.

Processing Flow (Condition Determination for 1 Scanning)

Figure 8:
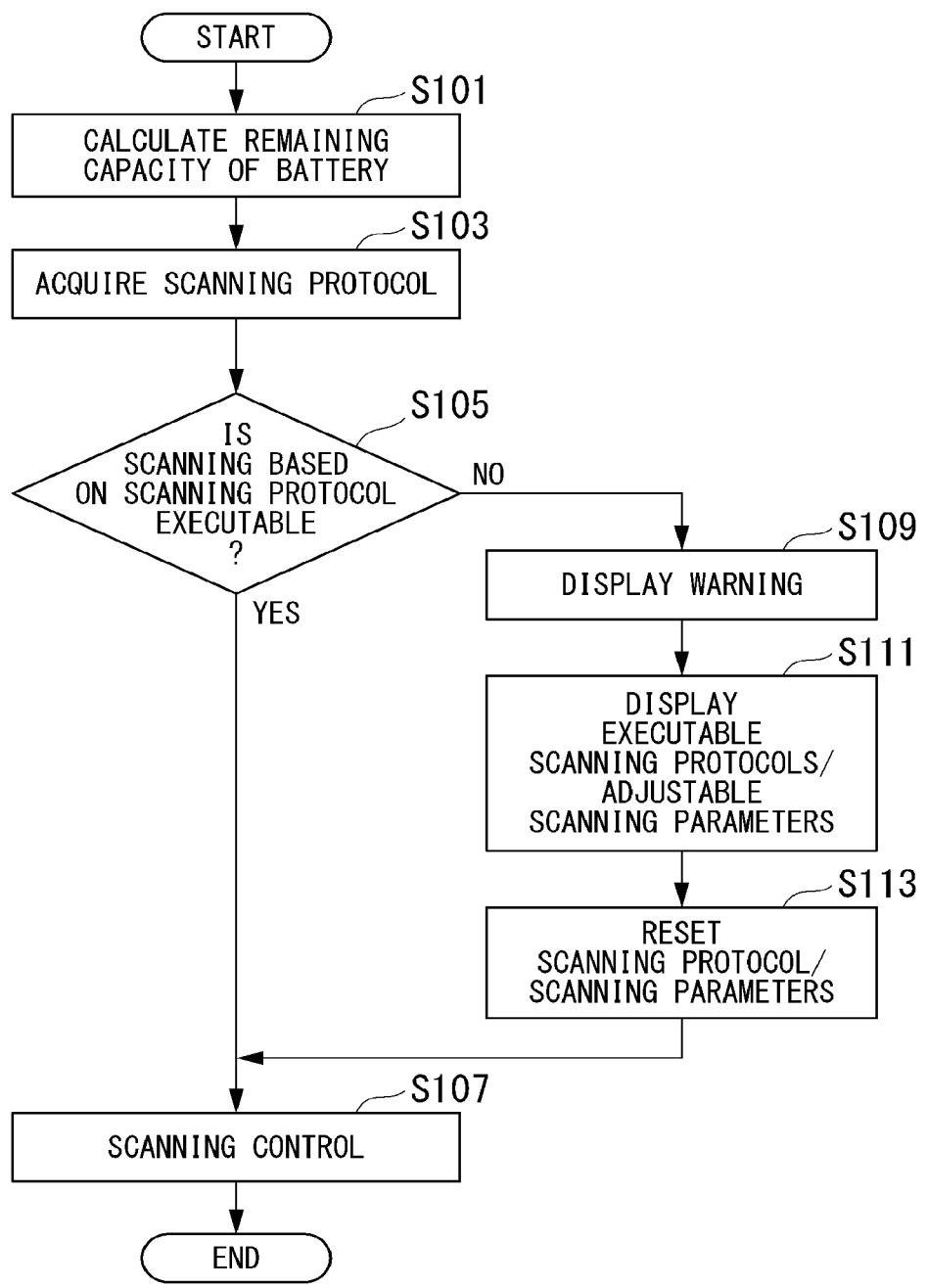
FIG. 8 is a flowchart showing an example of processing of processing circuitry 50 of a console device 40 according to the embodiment.

Hereinafter, a processing flow of the processing circuitry 50 of the console device 40 will be described. FIG. 8 is a flowchart showing an example of processing of the processing circuitry 50 of the console device 40. When the X-ray CT apparatus 1 scans the examination subject P, an operator of the X-ray CT apparatus 1 creates a scanning protocol with respect to scanning scheduled to be executed henceforward. Hereinafter, description will be given on the assumption that the scanning protocol has been created and stored in the memory 41.

First, the remaining capacity-monitoring function 57 of the processing circuitry 50 calculates the remaining capacity of the battery 14 on the basis of data of a voltage value and a current value of the battery 14 transmitted from the sensor 21 of the detection device 15 (step S101). For example, the remaining capacity-monitoring function 57 calculates the SOC of the battery 14 on the basis of the open-circuit voltage of the battery 14 and an integrated value of the charging/discharging current of the battery 14.

Next, the determination function 58 acquires the scanning protocol from the memory 41 (step S103). Then, the determination function 58 determines whether scanning based on the acquired scanning protocol can be executed with the calculated remaining capacity of the battery 14 (step S105). For example, when a scanning range included in the scanning protocol is "the whole body of the examination subject P" and the calculated remaining capacity of the battery 14 is equal to or greater than a capacity necessary to execute scanning in the scanning range, the determination function 58 determines that scanning based on the acquired scanning protocol can be executed. When the determination function 58 determines that scanning based on the acquired scanning protocol can be executed, the scanning control function 55 executes scanning control (step S107). Accordingly, scanning using the battery 14 as a driving source is executed in the gantry 10.

On the other hand, when the scanning range included in the scanning protocol is "the whole body of the examination subject P," the calculated remaining capacity of the battery 14 is less than the capacity necessary to execute scanning in the scanning range (that is, when the battery capacity is insufficient), and the determination function 58 determines that scanning based on the scanning protocol cannot be executed, for example, the warning function 59 causes the display 42 to display a warning representing that scanning scheduled to be executed cannot be executed (step S109).

The determination function 58 causes the display 42 to display executable scanning protocols and/or adjustable scanning parameters after the warning is displayed on the display 42 or when the warning is displayed (step S111).

Figure 9:
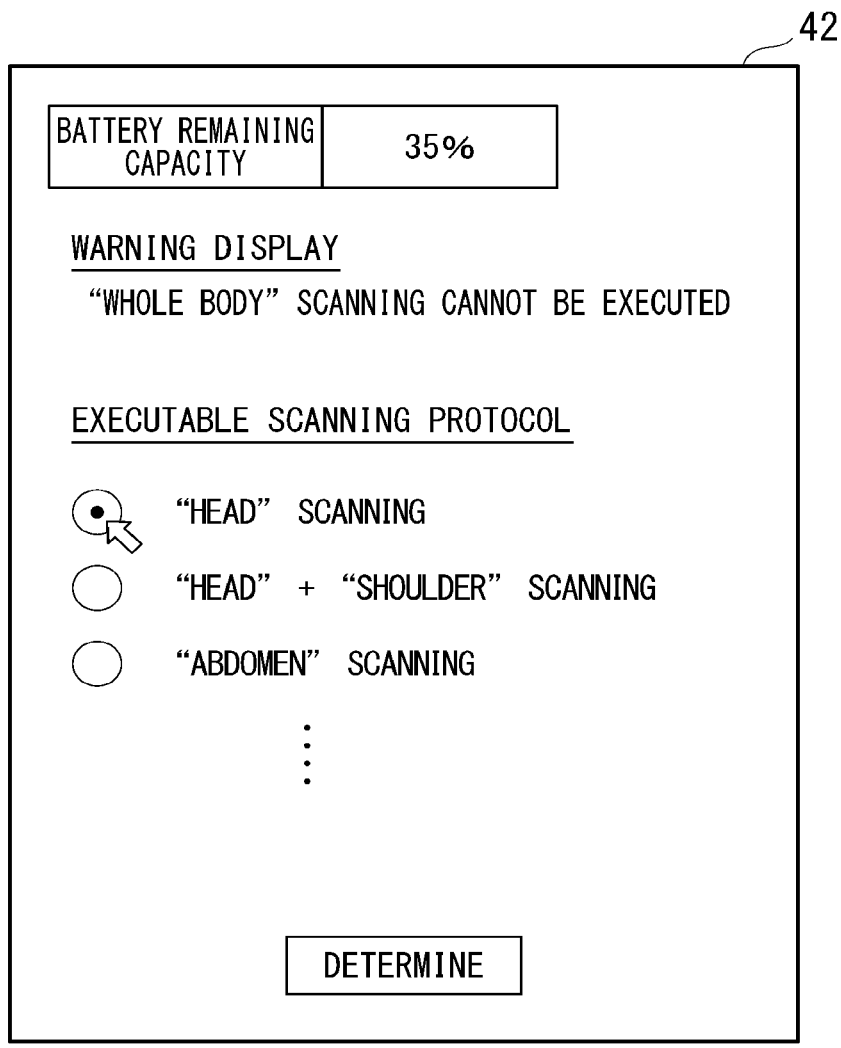
FIG. 9 is a diagram showing an example of a warning and executable scanning protocols displayed on a display 42 according to the embodiment.

FIG. 9 is a diagram showing an example of a warning and executable scanning protocols displayed on the display 42. In the example of FIG. 9, text of ""whole body" scanning cannot be executed" is displayed as a warning and ""head" scanning," ""head"+"shoulder" scanning", ""abdomen" scanning" and the like are displayed as executable scanning protocols. That is, the determination function 58 displays scanning protocols that has lower power consumption than scanning having "whole body" of the examination subject P as a scanning range which has been initially scheduled to be executed and can be executed with the calculated remaining capacity of the battery 14. In addition, an indication by which selection of an operator can be received (e.g., a "radio button") is displayed along with the executable scanning protocols in the example of FIG. 9. The operator can designate a scanning protocol that can be executed with the current remaining capacity of the battery 14 by designating any of the executable scanning protocols.

Figure 10:
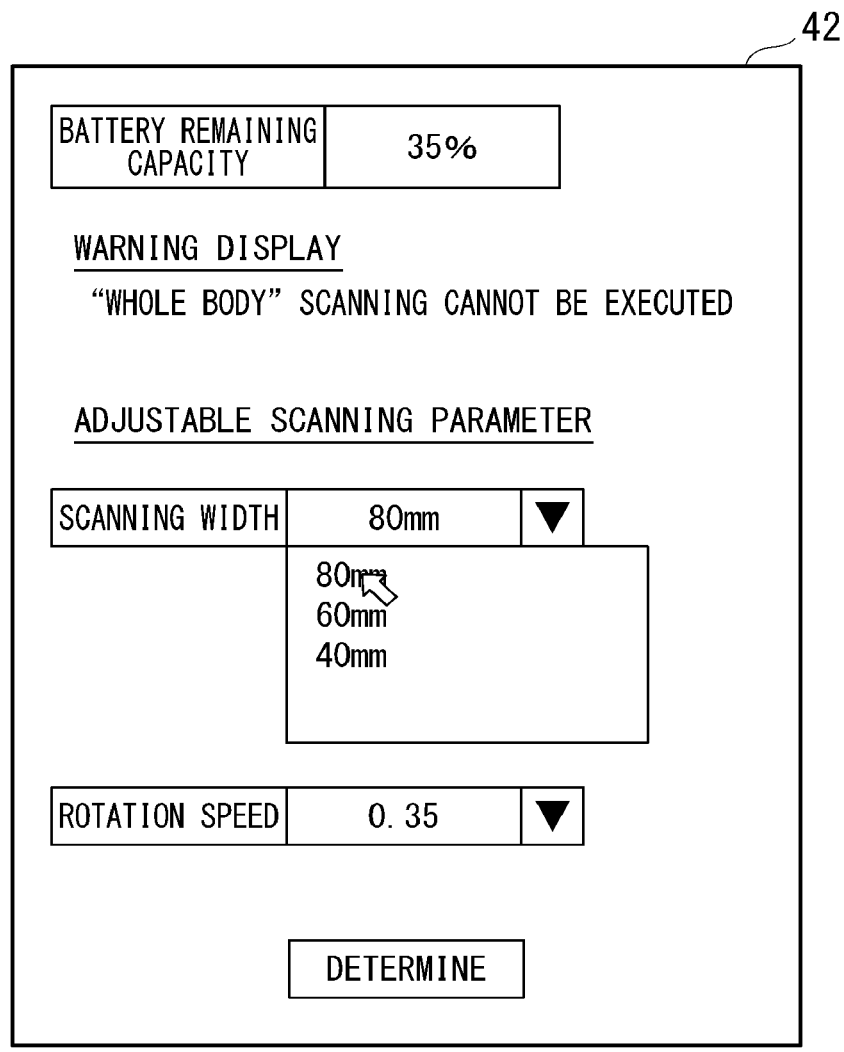
FIG. 10 is a diagram showing an example of a warning and adjustable scanning parameters displayed on the display 42 according to the embodiment.

FIG. 10 is a diagram showing an example of a warning and adjustable scanning parameters displayed on the display 42. In the example of FIG. 10, text of ""whole body" scanning cannot be executed" is displayed as a warning and "scanning width," "rotation speed" and the like are displayed as adjustable scanning parameters. That is, the determination function 58 does not change a scanning protocol that has been initially scheduled to be executed and causes the display 42 to display a screen through which scanning parameters included in this scanning protocol can be adjusted. For example, "80 mm," "60 mm" and "40 mm" in a list of scanning widths that can be executed with the current remaining capacity of the battery 14 are displayed in a mode (e.g., "pulldown") in which selection of the operator can be received in the example of FIG. 10. The operator can designate a value of a specific scanning parameter from among the displayed list to designate the scanning parameter that can be executed with the current remaining capacity of the battery 14.

Next, the determination function 58 resets a scanning protocol and/or scanning parameters designated by the operator as a scanning protocol and/or scanning parameters scheduled to be executed (step S113). Subsequently, the scanning control function 55 executes scanning control based on the reset scanning protocol and/or scanning parameters (step S107). Accordingly, scanning using the battery 14 as a driving source is executed in the gantry 10. In this manner, processing of this flowchart ends.

When a high-voltage generation device capable of performing power supply through a slip ring is provided in the gantry 10 in addition to the battery 14, the determination function 58 may display a screen through which an instruction for performing power supply through the slip ring is received instead of or in addition to displaying executable scanning protocols and/or adjustable scanning parameters through the display 42. The operator can supplement insufficient electric power from the remaining capacity of the battery 14 through power supply via the slip ring by inputting the instruction for performing power supply through the slip ring.

In addition, when a power transmitter of a contactless type charging device is disposed to surround the rotary frame 16, the determination function 58 may display a screen through which an instruction for performing charging through the contactless type charging device during scanning is received instead of or in addition to displaying executable scanning protocols and/or adjustable scanning parameters through the display 42. The operator can supplement insufficient electric power from the remaining capacity of the battery 14 through charging during scanning by inputting the instruction for performing charging through the contactless type charging device during scanning.

Processing Flow (Condition Determination for Multiple Scanning Operations)

Figure 11:
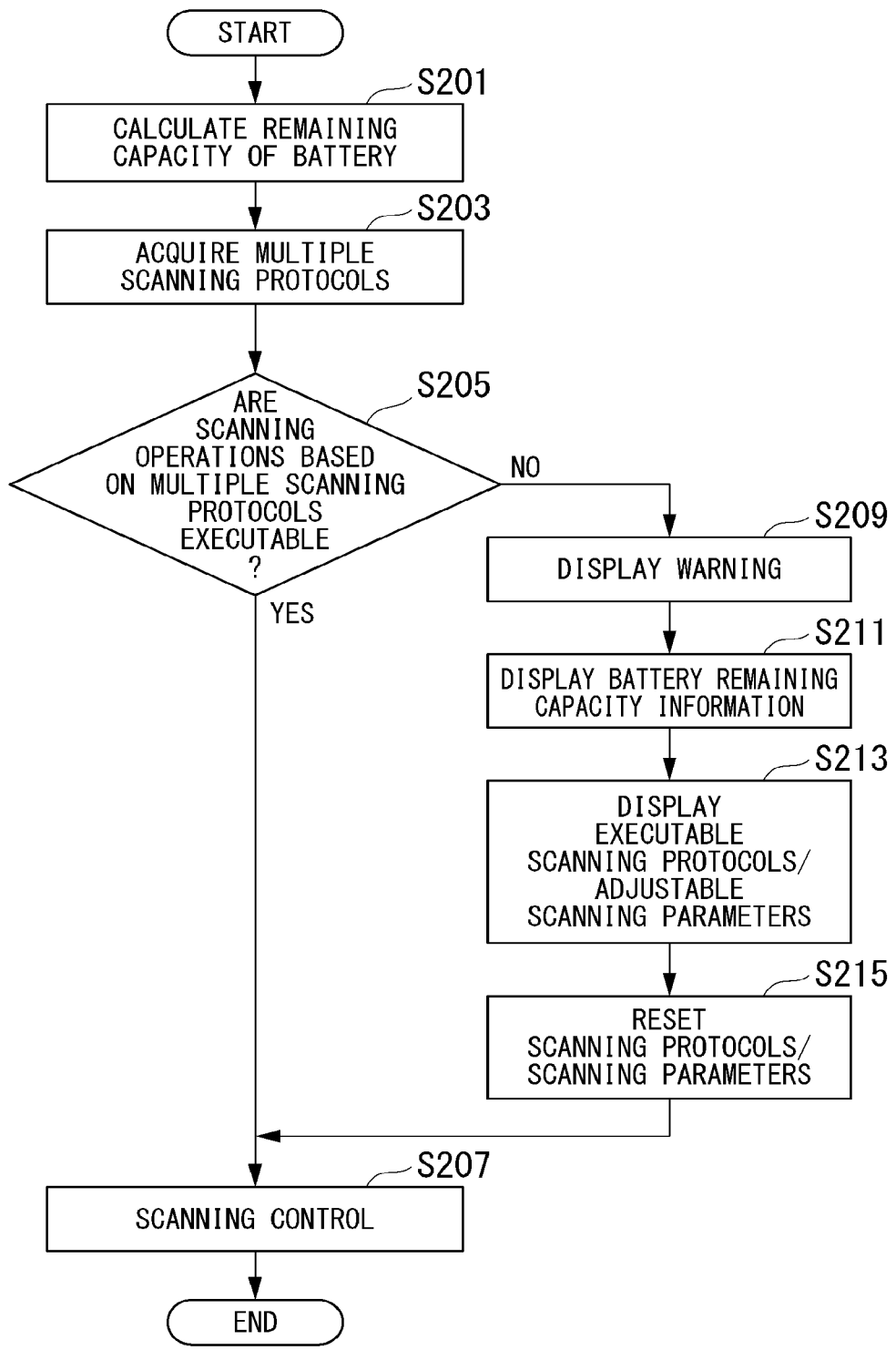
FIG. 11 is a flowchart showing another example of processing of the processing circuitry 50 of the console device 40 according to the embodiment.

FIG. 11 is a flowchart showing another example of processing of the processing circuitry 50 of the console device 40. When the X-ray CT apparatus 11 scans the examination subject P, the operator of the X-ray CT apparatus 1 creates a scanning protocol to be executed henceforward. This scanning protocol is created for each examination subject P. Scanning for many examination subjects P is executed daily in medical facilities and the like. Accordingly, there are cases in which, for example, an operator makes a scanning plan in the morning of a day when scanning is performed on the basis of a plurality of scanning protocols scheduled to be performed on the day. Hereinafter, description will be given on the assumption that the plurality of scanning protocols have been created and stored in the memory 41.

First, the remaining capacity-monitoring function 57 of the processing circuitry 50 calculates the remaining capacity of the battery 14 on the basis of data of a voltage value and a current value of the battery 14 transmitted from the sensor 21 of the detection device 15 (step S201). For example, the remaining capacity-monitoring function 57 may calculate the SOC of the battery 14 on the basis of the open-circuit voltage of the battery 14 and an integrated value of the charging/discharging current of the battery 14.

Next, the determination function 58 acquires a plurality of scanning protocols from the memory 41 (step S203). Then, the determination function 58 determines whether scanning operations based on the plurality of acquired scanning protocols can be executed with the calculated remaining capacity of the battery 14 (step S205). For example, when there are 10 scanning protocols and the calculated remaining capacity of the battery 14 is equal to or greater than a capacity necessary to execute scanning operations based on these 10 scanning protocols, the determination function 58 determines that the scanning operations based on the plurality of acquired scanning protocols can be executed. In this case, the determination function 58 may cause the display 42 to display an indication representing that the scanning operations based on the plurality of acquired scanning protocols can be executed. When the determination function 58 determines that the scanning operations based on the acquired scanning protocols can be executed, the scanning control function 55 executes scanning control (step S207). Accordingly, scanning using the battery 14 as a driving source is executed in the gantry 10.

On the other hand, when there are 10 scanning protocols, the calculated remaining capacity of the battery 14 is less than the capacity necessary to execute the scanning operations based on these 10 scanning protocols (that is, the battery capacity is insufficient), and the determination function 58 determines that the scanning operations based on the plurality of scanning protocols cannot be executed, the warning function 59 causes the display 42 to display a warning representing that scanning scheduled to be executed cannot be executed (step S209).

Next, the estimation function 60 estimates change in the remaining capacity of the battery 14 on the basis of the calculated remaining capacity of the battery 14 and the plurality of acquired scanning protocols and causes the display 42 to display battery remaining capacity information (step S211). The battery remaining capacity information represents, for example, a timing at which the remaining capacity of the battery 14 becomes less than a predetermined threshold value (e.g., zero) (e.g., a time at which the remaining capacity of the battery 14 becomes zero, an operable time until the remaining capacity becomes zero, and a scanning protocol that cannot be executed among a plurality of scanning protocols arranged in a time series) when scanning operations based on the plurality of acquired scanning protocols are sequentially executed.

Next, the determination function 58 causes the display 42 to display executable scanning protocols and/or adjustable scanning parameters after a warning and the battery remaining capacity information are displayed on the display 42 or along therewith (step S213). Here, the operator can select a scanning protocol to be preferentially executed. Further, the operator can make a plan for charging the battery 14.

Next, the determination function 58 resets a scanning protocol and/or scanning parameters designated by the operator as a scanning protocol scheduled to be executed (step S215). Subsequently, the scanning control function 55 executes scanning control based on the reset scanning protocol (step S207). Accordingly, scanning using the battery 14 as a driving source is executed in the gantry 10. In this manner, processing of this flowchart ends.

Processing Flow (Charging of Battery 14)

Figure 12:
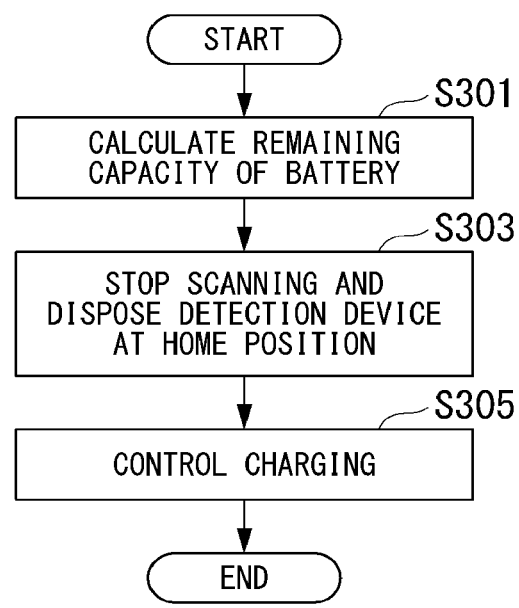
FIG. 12 is a flowchart showing an example of charging processing of the processing circuitry 50 of the console device 40 according to the embodiment.

FIG. 12 is a flowchart showing an example of charging processing of the processing circuitry 50 of the console device 40. First, the remaining capacity-monitoring function 57 of the processing circuitry 50 calculates the remaining capacity of the battery 14 on the basis of data of a voltage value and a current value of the battery 14 transmitted from the sensor 21 of the detection device 15 (step S301). For example, the remaining capacity-monitoring function 57 calculates the SOC of the battery 14 on the basis of the open-circuit voltage of the battery 14 and an integrated value of the charging/discharging current of the battery 14.

Next, when a charging instruction is received from the operator through an input interface or the remaining capacity of the battery 14 becomes less than a predetermined threshold value, the system control function 51 stops scanning and rotates the rotary frame 16 such that the detection device 15 is disposed at the home position (step S303).

Next, the system control function 51 controls the charging device 18 such that it charges the battery 14 (step S305). Accordingly, the charging device 18 supplies electric power to the battery 14 and charging of the battery 14 is executed. Accordingly, processing of this flowchart ends.

According to the X-ray CT apparatus 1 of the above-described embodiment, it is possible to reduce the number of man-hours and costs of maintenance such as replacement of a slip ring by driving the rotating body using the battery. In addition, it is possible to prevent the picture quality of a scanned image from deteriorating due to noise generated during power supply because it is not necessary to use a switching power supply and the like. Accordingly, it is possible to prevent picture quality deterioration of a scanned image even in the case of a low X-ray dose or low count.

Furthermore, it is possible to decrease a degree of difficulty in circuit design and reduce manufacture costs because it is not necessary to use a high-performance switching power supply, a linear regulator, a noise filter, and the like which can reduce noise.

Although a case in which the processing circuitry 50 of the console device 40 performs battery remaining capacity monitoring control and the like is exemplified in the above-described embodiment, the present invention is not limited thereto. For example, battery remaining capacity monitoring control and the like may be performed by the control device 17 provided in the gantry 10 or a controller provided in each DAS substrate 26 of the DAS 20.

Figure 13:
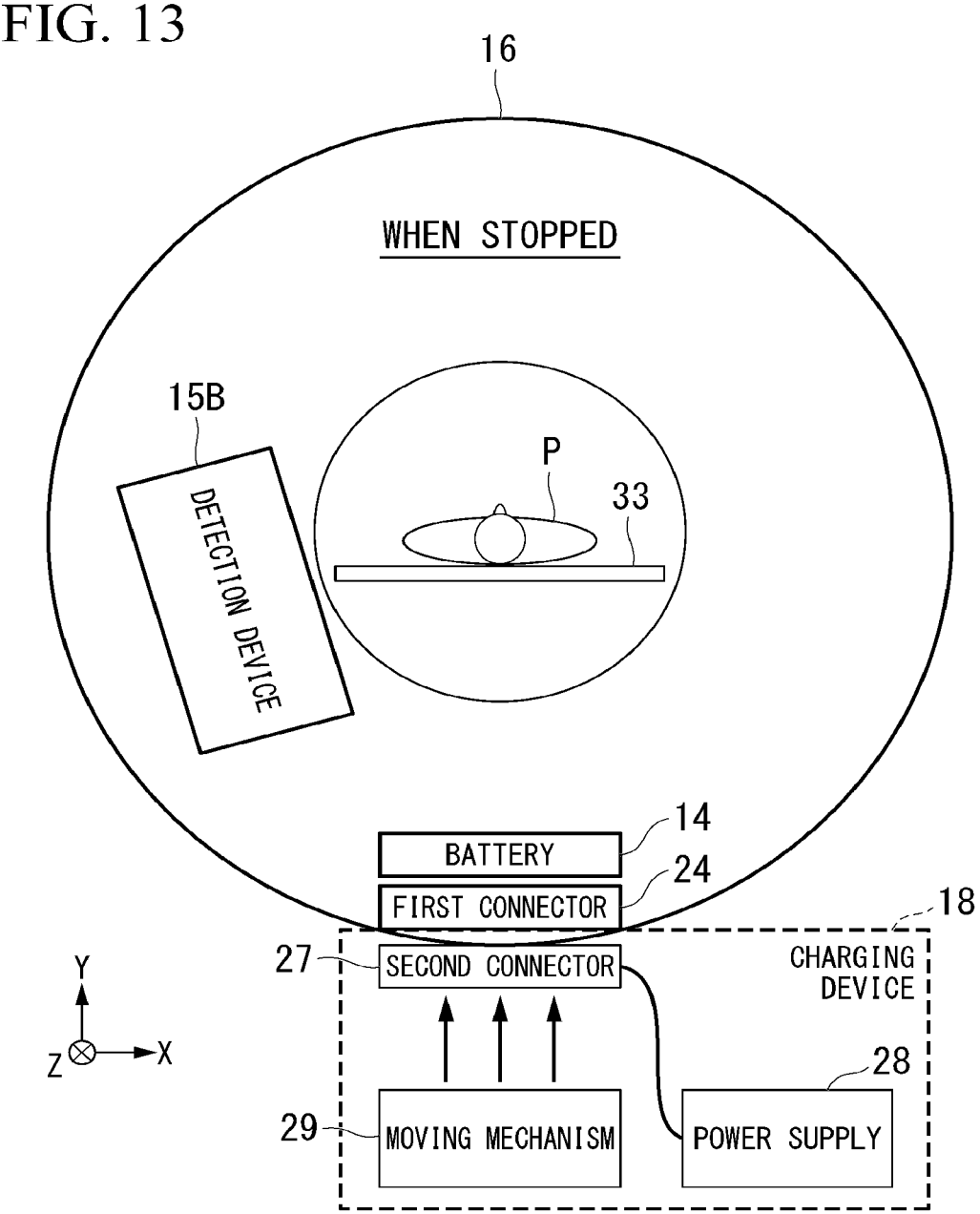
FIG. 13 is a diagram showing a state when charging is performed in the contact type charging device 18 according to the embodiment.

In addition, although a case in which the battery 14 is provided in the detection device 15 is exemplified in the above-described embodiment, the present invention is not limited thereto. For example, the battery 14 and the first connector 24 may be provided in the rotary frame 16 instead of a detection device 15B, as shown in FIG. 13. Charging according to the contact type charging device 18 may be performed when the battery 14 and the first connector 24 are positioned at the home position. Furthermore, the charging method using the contactless type charging device 18A as shown in FIG. 6 may be employed.

According to the X-ray CT apparatus 1 of the above-described embodiment, it is possible to reduce the number of man-hours and costs of maintenance such as replacement of a slip ring, and the like by including the X-ray tube 11, the X-ray detector 19 which detects X rays output from the X-ray tube 11, the data processor 20 which processes a signal output from the X-ray detector 19, the battery 14 which supplies electric power to the data processor 20, a rotating body 16 which rotatably supports the X-ray tube 11 and the X-ray detector 19 such that the X-ray tube 11 faces the X-ray detector 19 and further rotatably supports the data processor 20 and the battery 14, the remaining capacity monitor 57 which monitors the remaining capacity of the battery 14, and the determiner 58 which determines scanning conditions on the basis of the remaining capacity.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT apparatus, comprising:
   an X-ray tube;
   an X-ray detector configured to detect X rays output from the X-ray tube;
   a data processor configured to process a signal output from the X-ray detector;
   a battery configured to supply electric power to the data processor;
   a rotating body configured to rotatably support the X-ray tube and the X-ray detector, the X-ray tube facing the X-ray detector, and further to rotatably support the data processor and the battery; and
   processing circuitry configured to
      monitor a remaining capacity of the battery,
      determine a scanning condition on the basis of the remaining capacity; and
      determine at least one candidate for an executable scanning protocol on the basis of the remaining capacity.

2. The X-ray CT apparatus according to claim 1, wherein the processing circuitry is configured to determine at least one scanning protocol executable with the remaining capacity as the at least one candidate and to cause a display device to display the determined at least one candidate in a case where the remaining capacity is less than a capacity necessary for a scanning protocol scheduled to be executed.

3. The X-ray CT apparatus according to claim 1, wherein the processing circuitry is configured to determine whether at least one scanning parameter included in a scanning protocol scheduled to be executed is applicable on the basis of the remaining capacity.

4. The X-ray CT apparatus according to claim 3, wherein the processing circuitry is configured to determine at least one candidate for the at least one scanning parameter executable with the remaining capacity and to cause a display device to display the determined at least one candidate in a case where the remaining capacity is less than a capacity necessary for the scanning protocol scheduled to be executed.

5. The X-ray CT apparatus according to claim 1, wherein the processing circuitry is configured to perform a warning display in a case where the processing circuitry determines that the scanning condition is inexecutable.

6. The X-ray CT apparatus according to claim 1, wherein the processing circuitry is configured to estimate a timing at which the remaining capacity of the battery will reach a predetermined threshold value on the basis of the remaining capacity in a case where a scanning protocol scheduled to be executed is executed.

7. The X-ray CT apparatus according to claim 1, further comprising:
   a power supply configured to supply electric power to the data processor in a case where the processing circuitry determines that the remaining capacity is less than a capacity necessary for a scanning protocol scheduled to be executed.

8. The X-ray CT apparatus according to claim 1, further comprising:
   a charging device disposed in a fixed part of the X-ray CT apparatus and configured to supply electric power to the battery when scanning of the X-ray CT apparatus stops.

9. The X-ray CT apparatus according to claim 8, further comprising:
   a first connector supported by the rotating body and connected to the battery, wherein
   the charging device comprises a second connector detachably connected to the first connector, and
   the charging device is configured to supply electric power to the battery by connecting the second connector to the first connector when scanning of the X-ray CT apparatus stops.

10. The X-ray CT apparatus according to claim 8, wherein
    the charging device comprises a power transmitter configured to transmit electric power to the battery in a contactless manner, and
    the X-ray CT apparatus further comprises a power receiver supported by the rotating body and configured to receive electric power transmitted from the power transmitter and to supply the electric power to the battery.

11. An X-ray CT apparatus, comprising:
    an X-ray tube;
    an X-ray detector configured to detect X rays output from the X-ray tube;
    a data processor configured to process a signal output from the X-ray detector;
    a battery configured to supply electric power to the data processor;
    a rotating body configured to rotatably support the X-ray tube and the X-ray detector, the X-ray tube facing the X-ray detector, and further to rotatably support the data processor and the battery; and
    processing circuitry configured to
       monitor a remaining capacity of the battery,
       determine a scanning condition on the basis of the remaining capacity, and
       perform a warning display in a case where the processing circuitry determines that the scanning condition is inexecutable.

12. An X-ray CT apparatus, comprising:
    an X-ray tube;
    an X-ray detector configured to detect X rays output from the X-ray tube;
    a data processor configured to process a signal output from the X-ray detector;
    a battery configured to supply electric power to the data processor;
    a rotating body configured to rotatably support the X-ray tube and the X-ray detector, the X-ray tube facing the X-ray detector, and further to rotatably support the data processor and the battery; and
    processing circuitry configured to
       monitor a remaining capacity of the battery,
       determine a scanning condition on the basis of the remaining capacity, and
       estimate a timing at which the remaining capacity of the battery will reach a predetermined threshold value on the basis of the remaining capacity in a case where a scanning protocol scheduled to be executed is executed.

* * * * *